(12) United States Patent
Ursella et al.

(10) Patent No.: US 11,428,648 B2
(45) Date of Patent: Aug. 30, 2022

(54) METHOD AND APPARATUS FOR PERFORMING A TOMOGRAPHIC EXAMINATION OF AN OBJECT

(71) Applicant: MICROTEC S.R.L., Bressanone (IT)

(72) Inventors: Enrico Ursella, Mestre (IT); Federico Giudiceandrea, Bressanone (IT)

(73) Assignee: MICROTEC S.R.L., Bressanone (IT)

( * ) Notice: Subject to any disclaimer, the term of this patent is extended or adjusted under 35 U.S.C. 154(b) by 91 days.

(21) Appl. No.: 17/072,982

(22) Filed: Oct. 16, 2020

(65) Prior Publication Data
US 2021/0116395 A1  Apr. 22, 2021

(30) Foreign Application Priority Data
Oct. 21, 2019  (IT) .................... 102019000019454

(51) Int. Cl.
*G01N 23/046* (2018.01)
*G06T 7/73* (2017.01)
(Continued)

(52) U.S. Cl.
CPC ......... *G01N 23/046* (2013.01); *G01N 23/083* (2013.01); *G01N 33/02* (2013.01);
(Continued)

(58) Field of Classification Search
CPC .... G01N 23/046; G01N 23/083; G01N 33/02; G01N 2223/04; G01N 2223/3306;
(Continued)

(56) References Cited

U.S. PATENT DOCUMENTS

| 4,989,225 A | 1/1991 | Gupta et al. |
| 4,989,925 A | 2/1991 | Kohno |

(Continued)

FOREIGN PATENT DOCUMENTS

| CN | 2874482 | 2/2007 |
| DE | 102012019851 | 4/2014 |

(Continued)

OTHER PUBLICATIONS

Piccolomini, E., et al., "The Conjugate Gradient Regularization Method in Computed Tomography Problems", Applied Mathematics and Computation, Elsevier, vol. 102 1999, pp. 87-99.
(Continued)

*Primary Examiner* — David P Porta
*Assistant Examiner* — Mamadou Faye
(74) *Attorney, Agent, or Firm* — Pearne & Gordon LLP (57) ABSTRACT

A method and a related apparatus for performing a tomographic examination of an object (2) which advances through an examination area (6), wherein the examination area (6) is irradiated with x-rays transversally to a motion trajectory of the object (2) and the residual intensity of the x-rays which have crossed the object (2) is repeatedly detected to obtain, for each detection, an electronic two-dimensional pixel map, the two-dimensional maps thus obtained being processed by a computer to obtain a three-dimensional tomographic reconstruction of the object (2); wherein, during the advancement, the object (2) is made or let rotate, at least partly uncontrolled, in such a way that the object (2) rotates around one or more rotation axes which are transversal both to the motion trajectory and to the propagation directions of the x-rays crossing it; and wherein a computer also determines the spatial position in which the object (2) is located relative to the one or more emitters (4) and/or the one or more detectors (5) at the instant when each
(Continued)

two-dimensional map is detected, and factors this in the tomographic reconstruction.

19 Claims, 2 Drawing Sheets

(51) Int. Cl.
    *G06T 7/246* (2017.01)
    *G01N 23/083* (2018.01)
    *G01N 33/02* (2006.01)
    *G06T 7/00* (2017.01)
    *G06T 11/00* (2006.01)

(52) U.S. Cl.
    CPC ............ *G06T 7/0004* (2013.01); *G06T 7/248* (2017.01); *G06T 7/74* (2017.01); *G06T 11/003* (2013.01); *G01N 2223/04* (2013.01); *G01N 2223/3306* (2013.01); *G01N 2223/3307* (2013.01); *G01N 2223/3308* (2013.01); *G01N 2223/419* (2013.01); *G01N 2223/601* (2013.01); *G06T 2207/10081* (2013.01); *G06T 2207/30128* (2013.01)

(58) Field of Classification Search
    CPC ... G01N 2223/3307; G01N 2223/3308; G01N 2223/419; G01N 2223/601; G01N 2207/10081; G01N 2207/30128; G01N 2211/428; G01N 2211/436; G06T 7/0004; G06T 7/248; G06T 7/74; G06T 11/003; G06T 11/006
    See application file for complete search history.

(56) References Cited

U.S. PATENT DOCUMENTS

| | | |
|---|---|---|
| 6,584,170 B2 | 2/2003 | Aust |
| 6,792,066 B1 | 9/2004 | Harder et al. |
| 8,031,833 B2 | 10/2011 | Lin et al. |
| 8,121,361 B2 | 2/2012 | Ernst et al. |
| 8,374,411 B2 | 2/2013 | Ernst et al. |
| 8,571,293 B2 | 7/2013 | Ernst et al. |
| 8,811,570 B2 | 8/2014 | Speller |
| 9,076,212 B2 | 7/2015 | Ernst et al. |
| 9,138,175 B2 | 8/2015 | Ernst et al. |
| 9,174,245 B2 | 11/2015 | Blanc |
| 9,867,549 B2 | 1/2018 | Ernst et al. |
| 2003/0031293 A1 | 2/2003 | Aust |
| 2005/0238219 A1 | 10/2005 | Roux et al. |
| 2007/0280508 A1 | 12/2007 | Ernst et al. |
| 2010/0121484 A1 | 5/2010 | Blanc |
| 2012/0224666 A1* | 9/2012 | Speller ............... G01T 1/1603 378/8 |
| 2012/0288143 A1 | 11/2012 | Ernst et al. |
| 2012/0330684 A1* | 12/2012 | Jacobs ............... G07F 11/005 604/404 |
| 2013/0188830 A1 | 7/2013 | Ernst et al. |
| 2014/0037174 A1 | 2/2014 | Ernst et al. |
| 2015/0227793 A1 | 8/2015 | Ernst et al. |
| 2016/0166205 A1 | 6/2016 | Ernst et al. |
| 2018/0249927 A1 | 9/2018 | Ernst et al. |
| 2019/0137651 A1* | 5/2019 | Bendahan ............ G01V 5/0058 |
| 2021/0084240 A1* | 3/2021 | Mao .................... G06K 9/6271 |
| 2021/0270755 A1* | 9/2021 | De Beenhouwer ..... G06T 7/001 |

FOREIGN PATENT DOCUMENTS

| | | |
|---|---|---|
| EP | 1983335 | 10/2008 |
| EP | 2261643 A1 | 2/2013 |
| EP | 3106863 | 12/2016 |
| EP | 1283417 | 7/2018 |
| FR | 2913850 A1 | 9/2008 |
| IT | 1385072 | 12/2010 |
| IT | 1398460 | 2/2013 |
| WO | 2005001775 A1 | 1/2005 |
| WO | 2007136745 | 11/2007 |
| WO | 2008104627 | 9/2008 |
| WO | 2011042750 A1 | 4/2011 |

OTHER PUBLICATIONS

Yang., C., et al., "Unified 3-D Structure and Projection Orientation Refinement Using Quasi-Newton Algorithm", Journal of Structural Biology, Elsevier, vol. 149, 2005, pp. 53-64.

Parkinson, D., "Automatic Alignment and Reconstruction of Images for Soft X-Ray Tomography", Journal of Structural Biology, vol. 177, 2012, pp. 259-266.

Katsevitch, A., et al., "Reduction of Irregular View-Sampling Artifacts in a Stationary Gantry CT Scanner", SPIE, vol. 11072, 2019, pp. 1-6.

Katsevitch, A., "Local Tomography and the Motion Estimation Problem", Society for Industrial and Applied Mathematics, vol. 4, No. 1, 2011, pp. 200-219.

Katsevitch, A, "Motion Compensation Local Tomography", Inverse Problems, vol. 24, 2008, pp. 1-22.

Goris, B., et al., "Measuring Lattice Strain in Three Dimensions Through Electron Microscopy", Electron Microscopy for Materials Research (EMAT), vol. 15, 2015, pp. 6996-7001.

Janssens, E., et al., "Neural Network Based X-Ray Tomography For Fast Inspection of Apples on a Conveyor Belt System", 2015 IEEE International Conference on Image Processing (ICIP), IEEE, 2015, pp. 917-921.

Van Dael, M., et al., "Comparison of Methods for Online Inspection of Apple Internal Quality", Conference of Industrial Computed Tomography, Belgium, 2017, pp. 1-7.

De Schryver, T., et al., "In-Line NDT With X-Ray CT Combining Sample Rotation and Translation", CDT&E International, Elsevier, vol. 84, 2016, pp. 89-98.

Katsevitch, A., "Improved Cone Beam Local Tomography", Institute of Physics Publishing, Inverse Problems, vol. 22, 2006, pp. 627-643.

Katsevitch, A., "Cone Beam Local Tomography", SIAM Journal on Applied Mathematics, vol. 59, No. 6, 1999, pp. 2224-2246.

Beister, M., et al., "Iterative Reconstruction Methods in X-Ray CT", Sciverse Science Direct, Elsevier, vol. 28, 2012, pp. 94-108.

Feldkamp, L.A., et al., "Practical Cone-Beam Algorithm", J. Op. Soc. Am. A., vol. 1, No. 6, Jun. 1984, pp. 612-619.

Marchand, E., et al., "Pose Estimation for Augmented Reality: A Hands-On Survey", IEEE Transactions On Visualization and Computer Graphics, vol. 22, No. 12, Dec. 2016, pp. 2633-2651.

Alves Pereira, L. et al., "Inline Discrete Tomography System: Application to Agricultural Product Inspection", Computers and Electronics in Agriculture, Elsevier, Amsterdam, The Netherlands, vol. 138, May 2, 2017, pp. 117-126; XP085024300.

Mitschke, M. et al., "Recovering the X-Ray Projection Geometry for Three-Dimensional Tomographic Reconstruction with Additional Sensors: Attached Camera Versus External Navigation System", Medical Image Analysis, vol. 7, No. 1, Mar. 2003, pp. 65-78, XP055303295.

Janssens, E., et al., "Fast Inline Inspection by Neural Network Based Filtered Backprojection: Application to Apple Inspection", Case Studies in Nondestructive Testing and Evaluation, vol. 6, Nov. 2016, pp. 14-20, XP055674918.

* cited by examiner

METHOD AND APPARATUS FOR PERFORMING A TOMOGRAPHIC EXAMINATION OF AN OBJECT

The present invention relates to a method and an apparatus for performing a tomographic examination of an object.

In the context of the present invention, "tomographic examination" means the reconstruction of a three-dimensional model formed by a plurality of voxels and related to the density of the object. In particular, each voxel may be associated both with values related to the absolute density of the object in that area and with values related to the density variation in that area (such as values representing the density gradient). In the context of the present description and the accompanying claims, the definition of three-dimensional model obtained by a tomographic examination also includes models that have approximations at a greater or smaller degree relative to the actual values; what matters is that the model is appropriate for the type of information to be obtained (for instance, even a very approximate assessment of local density variation may be sufficient for detecting the presence or absence of solid foreign objects in yoghurt jar).

In particular, the present invention has been developed for performing industrial-level tomographic examinations, in particular in plants where productivity is very high and where products must undergo some kind of testing without this impacting on the average speed at which products are advanced along a production line (therefore, non-stop). By way of example, the present invention may be used to perform tomographic examinations of food products (fruit, bread, foodstuffs packaged in jars and cans) in order to verify their internal quality or to check for the absence of unwanted contaminants (such as pieces of plastic or glass), or to examine 3D-printed products (for instance, to check their internal structure, which would otherwise be inaccessible), etc.

Currently, tomographic systems are mainly divided into rotor-based systems, which are generally used in medicine, and rotating-object-based systems.

In the former, the rotor is a mechanical structure on which both the x-ray source and the detector are mounted, with the whole unit moving altogether around the object to be scanned, which in turn remains motionless or moves along one axis.

In the latter, both the x-ray source and the detector remain motionless, whereas the object must be moved in a precisely controlled manner inside the irradiated area.

Rotor-based systems are costly due to the need to rotate sophisticated equipment; moreover, the rotor usually is a large structure that cannot easily be installed around the area in which the objects to be scanned are to pass.

Rotating-object-based systems require that the object to be scanned is locked on a system that rotates (and in case translates) the object in a precise and predetermined manner. Generally, the complication of having to position and lock in the object to be scanned, renders these systems of little use in production lines and generally unsuitable for industrial plants that require high productivity. Indeed, the few systems proposed up to now require a mechanical arm, or another equivalent device, to grasp the item both in order to load it onto and unload it from the measurement system.

It also bears remembering that, for medical applications, certain techniques have been developed in the past to try to address the issue of a person's internal organs moving while the tomography is being performed. This issue has been addressed in publications including the following:

Piccolomini, Elena Loli, and Fabiana Zama. "The conjugate gradient regularization method in computed tomography problems." Applied mathematics and computation 102.1 (1999): 87-99;

Yang, Chao, Esmond G. Ng, and Pawel A. Penczek. "Unified 3-D structure and projection orientation refinement using quasi-Newton algorithm." Journal of structural biology 149.1 (2005): 53-64;

Parkinson, Dilworth Y., et al. "Automatic alignment and reconstruction of images for soft X-ray tomography." Journal of structural biology 177.2 (2012): 259-266;

Katsevich, Alexander, et al. "Reduction of irregular view-sampling artifacts in a stationary gantry CT scanner." 15th International Meeting on Fully Three-Dimensional Image Reconstruction in Radiology and Nuclear Medicine. Vol. 11072. International Society for Optics and Photonics, 2019;

Katsevich, Alexander, Michael Silver, and Alexander Zamyatin. "Local tomography and the motion estimation problem." SIAM Journal on Imaging Sciences 4.1 (2011): 200-219;

Katsevich, Alexander. "Motion compensated local tomography." Inverse Problems 24.4 (2008): 045012;

Goris, Bart, et al. "Measuring lattice strain in three dimensions through electron microscopy." Nano letters 15.10 (2015): 6996-7001;

On the one hand, all of these publications consider the use of rotating-rotor tomography, while on the other hand they take the assumption that the internal organs are objects with a limited and rigid motion. Moreover, every case addressed in the articles cited above looks at the potential for small, unwanted movements, which are—to all intents and purposes—regarded as problematic. Rotating-rotor-based medical tomographs are also described in patent documents U.S. Pat. No. 6,792,066, WO 2005/001775 and WO 2007/136745. Examples of publications relating to fixed-source, rotating-object tomographs include the following:

Janssens, Eline, et al. "Neural network based X-ray tomography for fast inspection of apples on a conveyor belt system." 2015 IEEE International Conference on Image Processing (ICIP). IEEE, 2015;

van Dael, Mattias, et al. "Comparison of methods for online inspection of apple internal quality." Online e-journal of nondestructive testing.--. 2017;

De Schryver, Thomas, et al. "In-line NDT with X-Ray CT combining sample rotation and translation." NDT & E International 84 (2016): 89-98.

Further examples of fixed-source, rotating-object tomographs are included in the following patent documents: U.S. Pat. No. 4,989,225, EP 1283417, CN 2874482U, WO 2008/104627, FR 2913850, EP 1983335, U.S. Pat. No. 8,031,833, WO 2011/42750, DE 102012019851 and EP 3106863.

In all cases described in the documents cited above, the motion of the object is entirely known, as the object is moved according to a predetermined pattern.

Nevertheless, none of the known solutions is usable in production lines that require high productivity, such as quality control lines for fruit (e.g. apples), control lines for industrial baked goods (e.g. bread loaves), check lines for packaged foodstuffs (e.g. jars of yoghurt), etc.

In this context, the technical purpose of the present invention is to implement a method and an apparatus for performing a tomographic examination of an object, which remedy the aforementioned drawbacks.

In particular, the technical purpose of the present invention is to develop a method and an apparatus for performing a tomographic examination of an object, which can be implemented on an industrial level.

A further technical purpose of the present invention is to develop a method and an apparatus for performing a tomographic examination of an object, which enable high productivity to be achieved.

Yet another technical purpose of the present invention is to develop a method and an apparatus for performing a tomographic examination of an object, which can be implemented without having to introduce particular structural complications into existing plants.

The technical purpose and the aims indicated above are substantially achieved by a method and an apparatus for performing a tomographic examination of an object in accordance with the contents of the accompanying claims.

The main inventive aspect of the present invention is based on the idea of combining a fixed tomograph firstly with an at least partly uncontrolled motion of the object, which would nevertheless ensure a sufficient number of different reciprocal positions between the tomograph and the object as to enable a tomographic reconstruction to be made, and secondly with a precise determination of the pose (i.e. the position and orientation) of the objects relative to the tomograph at the instant each radiographic image is detected. As regards the motion of the objects, the idea underlying the present invention was to combine a longitudinal motion of the objects to be examined, such as those commonly adopted in various industrial production lines, with the condition of causing, or simply allowing, the objects to rotate relative to the x-rays crossing them.

The fixed tomograph must therefore be of a size which allows a plurality of radiographic images of the objects to be successively captured, tracking the objects along part of their (advantageously longitudinal) advancement.

The trick of identifying, for each radiographic image captured, the relative position where the object is (if defined at the capture time) or was (if defined after the capture time) located at the instant when the radiographic image was captured then enables this partly-random sequence of radiographic images to be used in an algorithm for tomographic reconstruction.

A tomographic reconstruction requires radiographic images of the object to be captured from a large number (typically hundreds) of different angles. For reconstruction to be possible, it is required that, for each captured tomographic image, the relative position of the source, the detector and the object when the radiographic image was captured is also known.

The method and the apparatus proposed by the present invention can therefore be seen as a kind of variant of rotating-object-based systems, but where the motion of the objects is at least partly uncontrolled.

By way of example, the present invention can be applied in the sector of examination of fruit (e.g. apples), where some motive systems already use biconical rollers (with converging conicity), which precisely control the longitudinal advancement of the fruit and which cause the apples, as they are advanced, to continuously roll on themselves to allow at least most of their outer surface to be observed by video cameras.

One of the ideas underlying the present invention is that a system capable of rolling an object as the latter moves between a detector and an x-ray emitter allows multiple radiographs of the object to be obtained from different angles. Nevertheless, a structure of this type does not, in itself, allow any tomographic reconstruction to be made using the radiographs captured, as the actual trajectory of the fruit-object is not known, or rather its positions relative to the source and detector while each radiograph was being captured are not known. Let us again use the example of an apple. Even if this advances while resting on a pair of biconical rollers positioned side-by-side, its rolling motion on the rollers means that, due to the irregularity of its outer surface, it moves in a complex combination of multiple rotations and translations, rather than moving in a single rotational motion around a single rotation axis (as required in known fixed tomographs).

The second basic idea underlying the present invention was therefore to replace the active system which precisely controls the position of the object to be examined, which is usual in the state of the art for fixed tomographs, with a passive system which is confined to identifying the position in which the object is or was located relative to the emitter and the detector when capturing each radiographic image.

As described in greater detail below, according with further innovative aspects of the present invention (each of which the applicant reserves the right herein to separately protect by filing subsequent patent applications, also as divisional applications), several technical solutions have been developed which enable the position of an object to be understood, and also several technical solutions that ensure that the object properly moves in an at least partly uncontrolled manner. These technical solutions may be used either alone or in combination with each other.

Further features and the advantages of the present invention will become more apparent from the following detailed description of several preferred, non-limiting embodiments of a method and an apparatus for performing a tomographic examination of an object according to the present invention, wherein reference will also made to the accompanying figures, in which.

Where technically possible, the descriptions below, when relating to the method that is the subject of the present invention, should be understood as also being applicable to the apparatus that is the subject of the present invention, and vice versa.

In the most general embodiment of the present invention, the method for performing a tomographic examination of an object first of all comprises an advancement step, during which the object is advanced along a motion trajectory through an examination area. Please note that the examination area may be either a single consecutive area or composed of several sub-areas, which need not be contiguous.

At least as the object is advanced in the examination area, an irradiation step is envisaged during which the examination area is irradiated with x-rays emitted by one or more emitters. Preferably, the one or more emitters emit a beam of divergent x-rays (a cone beam).

According to the present invention, the position of the one or more emitters is kept fixed relative to the examination area, as is that of the one or more x-ray detectors, which face the one or more emitters and are arranged at the opposite side of the examination area.

In a first preferred embodiment, the one or more emitters and the one or more x-ray detectors face each other horizontally. In a second preferred embodiment, the one or more emitters and the one or more x-ray detectors face each other vertically.

During the advancement step, an object rotation step is envisaged, which may be performed either by actively making the object rotate or by letting it rotate (i.e. by not impeding the object from rotating under the forces to which it is subjected). According to the main innovative aspect of the present invention, the rotation step envisages that the rotation of the object is partly uncontrolled. Advantageously, the rotation step is performed by making or letting the object rotate in such a way that the object rotates around one or more rotation axes which are transversal both to the motion trajectory and to the propagation directions of the x-rays crossing it; in other words, in such a way that the object changes its angular position at least relative to a rotation axis which is both transversal to the motion trajectory and transversal to a half-line leaving a central point of the emitter by which it is irradiated and which crosses a centre of gravity of the object itself. Advantageously, the one or more rotation axes are inclined at an angle of between 40° and 90° relative to the motion trajectory (with this angle understood to mean the minimum angle between the rotation axis and a straight line tangential to the motion trajectory at that point). It should be noted that, for complex rotations in which the instant rotation axis changes from moment to moment (e.g. due to the surface characteristics of the object rolling on a support), it is not necessary for each instant rotation axis to comply at all moments with the above conditions relating to the angle relative to the motion trajectory; it is enough for just one of the instant rotation axes to comply. In most applications, however, the rotation axis will be either vertical (e.g. where the emitters and receivers are horizontally facing) or horizontal (e.g. where the emitters and receivers are vertically facing). Some embodiments are shown in the accompanying figures, as described below with reference to the apparatus.

However, depending on the specific application, the motion to which each object will be subject in order for the desired rotation to be obtained relative to the x-rays crossing it may be more complex or less complex. For instance, where the object is an apple carried on a biconical roller conveyor, the motion—where referred to a reference system on the one or more emitters—will comprise both instant rotations around multiple axes and translations.

In the preferred embodiment, divergent-beam emitters are preferably used and combined with detectors which, overall, have a relatively high length parallel to the motion trajectory, which is at least sufficient to let the object rotate on itself, in the time period necessary for going through the examination area, up to at least the minimum angle required for the tomographic reconstruction to be processed (generally 180° plus the angle underlying the object itself).

As the object is advanced through the examination area, a plurality of detection steps successively performed using the one or more fixed x-ray detectors is envisaged. During each detection step, the residual intensity of the x-rays which have crossed the object placed in the examination area is detected to obtain, for each detection, a corresponding two-dimensional pixel map representing the density of the object crossed by the x-rays (in other words, a computerised radiography of the object is performed); in general, at each detection, the object will be differently orientated relative to the propagation direction of the x-rays with which it is irradiated.

Each detection step is combined with a memorisation step, in which each detected two-dimensional map is memorised in an electronic memory using a computer.

According to a further innovative aspect of the present invention, the method comprises a localisation step performed by a computer (which may be the same as, or different to, that performing other steps), in which it is determined the spatial position (pose) of the object when each two-dimensional map is detected. This localisation step can be performed either at the same time as, or subsequent to, the detection step in which the related two-dimensional map is detected.

Depending on the embodiments, the spatial position, as determined during the localisation step, can be an absolute spatial position relative to a reference system (six degrees of freedom—three translations and three rotations) or a simplified spatial position which takes into account only some degrees of freedom. For example, in some embodiments it is enough to determine only the distance of the rotation axis from the emitter (or from the detector) and the angular position of the object around the rotation axis (relative to a predetermined angular position—e.g. the angular position of the object when the first two-dimensional map was detected).

In general, however, it is required to determine enough information as to link the detected two-dimensional map to the angular orientation of the object (in order to understand the direction in which the x-rays impact against the object) and to the size of the object or to its distance from the emitter or detector (for divergent x-ray beams, the size of the two-dimensional map depends on both the size of the object and its distance from the emitter and receiver).

To perform an appropriate tomographic reconstruction, the detection step should be repeated on each object as many times as it takes until a sufficient number of radiographs (electronic two-dimensional maps) have been obtained by observing the object from different angles (generally, at least one hundred different radiographs should be detected, although fewer or more radiographs may be necessary depending on the given case).

Once the detection steps are complete, the method envisages a processing step in which the two-dimensional maps thus obtained (not necessary all of them) are processed by a computer to obtain the three-dimensional tomographic reconstruction of the object. The processing phase is performed by the computer by factoring in, for each two-dimensional map, the corresponding spatial position of the object as determined in the localisation step.

Since, as mentioned above, the two-dimensional maps have been obtained in a manner which is at least partly uncontrolled, in the processing step it is not possible to apply just any of the known tomographic reconstruction techniques. Indeed, only some of these work with generic trajectories of the object (i.e. the overall motion of the object in the examination area), but most of them work for specifically defined trajectories only.

One possible approach is therefore to use the "local tomography" technique, which can be adapted to any type of trajectory. This is a relatively quick and straightforward algorithm that enables to obtain a three-dimensional tomographic image which represents the density derivative of the object, differently from more common reconstruction techniques which set out to calculate actual density. For more details on implementing "local tomography", see:

Katsevich, Alexander. "Improved cone beam local tomography." Inverse Problems 22.2 (2006): 627; and Katsevich, Alexander. "Cone beam local tomography." SIAM Journal on Applied Mathematics 59.6 (1999): 2224-2246;

the content of which is incorporated herein by reference.

In addition to being extremely flexible in terms of the trajectories that may be used, this technique is also particularly efficient in computational terms. In a nutshell, it involves filtering each two-dimensional map (or radiographic image; i.e. each projection on the x-ray detector) using a filter which performs the second derivative, and then backprojecting the projections into the voxels of interest. The disadvantage of this approach is that, instead of producing an image which represents the density of each voxel, it can only produce a version which represents the density derivative. Nevertheless, this reconstruction is more than adequate for many analyses of industrial interest. One possible issue, for instance, involves finding glass contaminants inside a jar of yoghurt or seeing whether the peel of an orange is attached to the fruit or not. In these cases, in order to check the characteristics searched for, the analysis of the three-dimensional images produced using the "local tomography" technique (which therefore represent density derivative) gives results which are analogous to those that would be obtained using a usual tomographic reconstruction.

Other approaches that can be used for the reconstruction based on an arbitrary trajectory include iterative algorithms, such as SIRT or ART.

For a sufficiently complete review of possible solutions, see:

Beister, Marcel, Daniel Kolditz, and Willi A. Kalender. "Iterative reconstruction methods in X-ray CT." Physica medica 28.2 (2012): 94-108;

the content of which is incorporated herein by reference.

However, these algorithms are quite demanding in computational terms.

Alternatively, a first reconstruction made using FDK-type algorithms can be used (see, for example, Feldkamp, Lee A., L. C. Davis, and James W. Kress. "Practical cone-beam algorithm." Josa a 1.6 (1984): 612-619, the content of which is incorporated herein by reference), which are not exact and require the trajectory to be approximated, and then the first reconstruction can be improved using some iterations of iterative algorithms.

As regards determining the angular position of the object when detecting the two-dimensional maps, according to one possible embodiment of the present invention the method comprises a capturing step in which a plurality of images of the object are successively captured as it is advanced along the motion trajectory. Advantageously, the images are captured using one or more digital video cameras. In particular, an image is preferably captured at basically the same time as detecting each two-dimensional map, and from an observation direction which is transversal to the x-ray propagation direction. For the most common applications, the observation direction will be either vertical (for horizontally facing emitters/detectors) or horizontal (for vertically facing emitters/detectors).

This approach can be used whenever the object has features that can be recognised in each image and whose position in each image is directly referable to the spatial position of the object.

Indeed, in this case the images can be compared with each other by the computer to determine one or more movements incurred by the object relative to a predefined reference position (e.g. its position when the first two-dimensional map was detected) or relative to its position in the previous image. Each movement can be defined as a set of translations and rotations relative to a reference system. The spatial position of the object relative to the predefined reference position, at the instant when each two-dimensional map was detected, can therefore be determined either directly or by "adding together" one or more intermediate movements. For the purposes of the subsequent tomographic reconstruction, it is advantageous to select, as the predefined reference position, the object position at the detection instant of the first two-dimensional map.

The localisation step is therefore performed using the images captured during the capturing step, to determine the spatial position in which the object is or was located at the instant when each two-dimensional map is/was detected.

As mentioned above, each movement incurred by the object may advantageously be determined by identifying, in each image, identification features peculiar to the object or applied to the object itself.

According to one embodiment, an easily identifiable marker can be applied to each object. Moreover, many objects already have similar markers; for instance, the QR code on the label of a can or a sticker affixed to an apple.

As regards the implementation of this technique for determining the spatial position of objects, it should be noted that there are many articles in literature which show how to obtain the pose (i.e. the position and the orientation) of a known object based on its image as captured using a calibrated video camera.

Details regarding its possible implementation are described in:

Marchand, Eric, Hideaki Uchiyama, and Fabien Spindler. "Pose estimation for augmented reality: a hands-on survey." IEEE transactions on visualization and computer graphics 22.12 (2015): 2633-2651 the content of which is incorporated herein by reference.

Even where there is no known marker on the surface of the object, an image of the object can still be used to measure its motion. Indeed, many "structure from motion" algorithms enable specific points to be identified within an image, enable these to be followed in images captured at different times and allow for the calculation of the rigid motion of the object to which the points belong. For instance, Marchand's article cited above describes several techniques that are useful for measuring the pose of an object from a sequence of images.

Patent IT 1385072, in the name of this applicant, whose content is incorporated herein by reference, describes the use of successive images of a fruit which rolls in an uncontrolled manner on its outer surface, as it advances, to determine the spatial position of the fruit (in this case, in order to reconstruct an overall image of the fruit appearance).

According to a different embodiment of the present invention, the method may comprise a step of three-dimensional scanning of the object (e.g. by laser triangulation), during which a plurality of three-dimensional scans of at least part of the object surface are successively captured as the object is advanced along the motion trajectory. In particular, a three-dimensional scan is preferably captured at basically the same time as detecting each two-dimensional map, and, preferably, by observing the object from an observation direction which is transversal to the x-ray propagation directions. Advantageously, scans are captured using one or more digital scanners.

This approach can be used whenever the object has surface features that can be recognised in each three-dimensional scan and whose position in each three-dimensional scan is directly referable to the spatial position of the object. Indeed, in this case the three-dimensional scans can be compared with each other by the computer to determine the one or more movements incurred by the object relative to the predefined reference position (e.g. its position when the first two-dimensional map was detected) or relative to its position in the previous image.

As when using images, the spatial position of the object relative to the predefined reference position, at the instant when each two-dimensional map was detected, can therefore be determined either directly or by "adding together" one or more intermediate movements.

In this case, the localisation step is performed using three-dimensional scans to determine the spatial position in which the object is or was located at the instant when each two-dimensional map is/was detected.

Patent IT 1398460, in the name of this applicant, whose content is incorporated herein by reference, describes the use of successive three-dimensional scans of the surface of a fruit which rolls in an uncontrolled manner on its outer surface, as it advances, to determine the spatial position of the fruit; in this case, however, the aim was to reconstruct the three-dimensional shape of the fruit's outer surface.

According to a further embodiment of the present invention, the localisation step is instead performed by the computer by directly analysing the three-dimensional maps detected. This is possible if identification elements that are x-ray visible can be identified in each two-dimensional map, where the identification elements are either peculiar to the object or have been associated to the object itself beforehand. Knowing the relative position of some identification elements (three points are sufficient, but two may also be sufficient if certain assumptions are made) and knowing their position in each two-dimensional map, this enables the position of the identification elements relative to the tomograph to be known. Identification elements may include tin pellets specifically applied to the packaging of all objects or features that are nevertheless present, such as the corner of a square package.

According to a further possible embodiment of the present invention, the localisation step is performed by the computer by performing the processing step several times, each time conjecturing a different sequence of the spatial positions of the object and estimating the precision of each conjectured spatial position, based on the outcome of the processing step.

In general, if a tomography is reconstructed based on incorrect information on the position of the object, an incorrect reconstruction will be obtained. Nevertheless, the use of some a priori information concerning the object to be reconstructed can make it possible to assess how far a reconstruction is plausibly correct or not.

The basic idea behind this embodiment of the present invention is therefore to perform the processing step a first time, based on a conjectured trajectory of the object (meaning the sequence of positions adopted by the object when each two-dimensional map is detected) that is considered as approximating the actual motion of the object, to verify its plausibility, to change the trajectory of the object a posteriori, and to iterate the steps of verification and change of trajectory, until a trajectory is obtained that enables a reconstruction to be obtained that is sufficiently correct for the predetermined purposes. This ensures that the actual trajectory will be sufficiently approximated with a sufficient margin of precision.

To make the calculation of the reconstruction plausibility quicker, one known option is to use the "local tomography" method described above.

When using "local tomography" (i.e. a reconstruction of the density derivative of the object), high derivative values are obtained at the edge of the object by inputting the correct trajectory, whereas lower values are obtained by inputting an incorrect trajectory, due to a "blurring" of the edge itself. The mere fact that the object is surrounded by air and therefore has an outer surface can therefore be used as a priori information concerning the object. The measure of the value of the reconstructed gradient provides a good measure as to the plausibility that the reconstruction is correct, and therefore of the plausibility that the trajectory being processed is also correct.

As regards the manners for advancing the object along the motion trajectory and for rotating the object relative to the x-rays, any means suited to this purpose may be used. Some non-restrictive examples are described below with reference to the apparatus described in the present invention.

If the object has a bottom base (such as foodstuff containers or bread loaves), then the object may run on a horizontal plane, the emitters and detectors may be horizontally facing (one opposite the other) and the rotation of the object occurs at least around one vertical axis.

If, on the other hand, the object does not have a bottom base, or is nevertheless able to roll on its own lateral surface (such as apples or similar fruit), then the object may run along a horizontal direction, the emitters and detectors may be vertically facing (one above the other) and the rotation of the object occurs at least around one horizontal axis.

Moving on to discuss the apparatus 1 for performing a tomographic examination of an object 2 according to the present invention, in general this is an apparatus 1 capable of operating at least one of the embodiments of the method described so far.

As with known fixed-tomograph apparatuses, the apparatus according to the present invention also comprises a supporting structure (not shown in the accompanying figures), with which it is associated at least one conveyor 3 capable of advancing an object 2 along a motion trajectory, one or more x-ray emitters 4 and one or more x-ray detectors 5. Both the one or more emitters 4 and the one or more detectors 5 are fixed and associated with the supporting structure. The detectors 5 also face the one or more x-ray emitters 4; an examination area 6 is defined between the one or more emitters 4 and the one or more detectors 5, through which a part of the motion trajectory of the object 2 develops. The motion trajectory is transversal to the propagation directions of the x-rays going from the one or more emitters 4 to the one or more detectors 5.

The device 1 comprises at least one computer (not shown) associated with the one or more detectors 5 to receive from them electronic data corresponding to two-dimensional pixel maps representative of the density of the object 2 crossed by the x-rays. The at least one computer is also capable of memorising said two-dimensional maps and is programmed to process the two-dimensional maps in order to obtain a three-dimensional tomographic reconstruction of the object 2.

Furthermore, means 7 for uncontrolled rotation are associated with the conveyor 3 and are able to cause an at least partly uncontrolled rotation of the object 2 as the object 2 is advanced along the motion trajectory, according to the ways described above in reference to the method.

Moreover, at least one electronic device is programmed to identify the spatial position in which the object 2 is located at the instant when each two-dimensional map is detected.

In a first embodiment, the electronic device comprises at least one computer (which may or may not be the same capable of performing other functions of the device 1), programmed to determine the spatial position in which the object 2 was located at the instant when each two-dimensional map was detected.

Advantageously, the computer can be programmed to determine this spatial position by directly processing the two-dimensional maps (if identification elements usable for this purpose are visible in those maps).

Alternatively, the electronic device may instead comprise one or more image capturing devices (advantageously digital video cameras—such as the video cameras 15 shown in the accompanying figures, if necessary combined with lighting systems 16), facing the examination area 6 and controlled in such a way as to successively capture a plurality of electronic images of the object 2 as it is advanced along the motion trajectory, and, advantageously, to capture one image at least at the instant when each two-dimensional map is detected. In this case, too, the electronic device also comprises at least one computer, this time programmed to determine the spatial position in which the object 2 was located at the instant when each two-dimensional map was detected, using the electronic images captured by the one or more image capture devices (according to the ways described above).

In one embodiment, the conveyor 3 comprises a plurality of supports which are movable along the motion trajectory; a unit for rotating the object 2 while on the support is associated with each support.

In particular, if the objects are able to roll on their outer surface (such as apples, oranges, peaches, etc.), the conveyor 3 may comprise at least two motive chains or belts 8, arranged side by side and parallel to one another, which run along the motion trajectory and hold up the supports. Each support comprises a pair of biconical rollers 9 mounted near to each other between the two motive chains or belts 8, and arranged so that their respective axes are perpendicular to the motion trajectory, in such a way that each object 2 can remain in the "cradle" defined by the two side-by-side biconical rollers 9. The unit for rotating the object 2 is advantageously arranged or shaped in such a way as to cause the rotation of at least one of the biconical rollers 9. By way of example, this can be a fixed stop 10, such as a rail or track, on which a projecting end 11 of one of the biconical rollers 9 of each support rolls. In another embodiment which is not shown, the conveyor 3 may comprise a track equipped with rotating roller or rotating ball, wherein the rotating rollers or the rotating balls are arranged and/or actuated, at least in groups, in a different manner, thus causing the object 2 to rotate on itself as it is advanced. In a further embodiment, the conveyor 3 may comprise both a longitudinal advancement system (such as a conveyor belt 12) supporting (preferably from below) the objects 2 and causing longitudinal advancement thereof, and one or more fixed stops arranged along the motion trajectory to intercept the object 2 as it advances, and to cause it to rotate on itself (the object 2 being caused to rotate by impacting against the stops).

Figure 1:
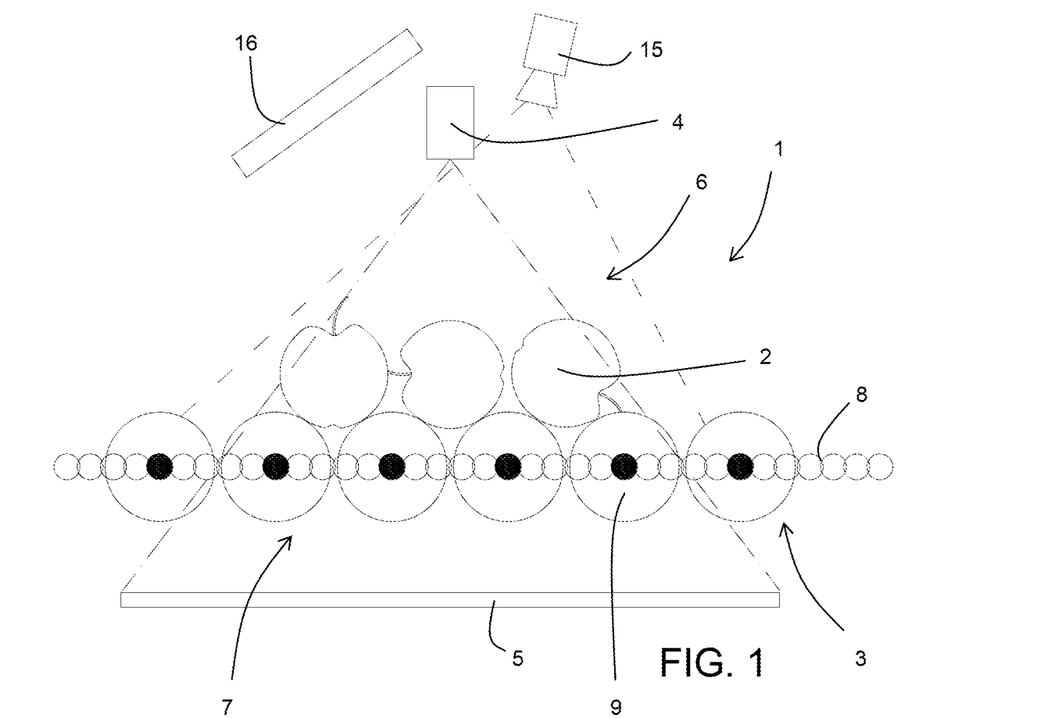
FIG. 1 shows a schematic lateral view of a first embodiment of a method and of an apparatus according to the present invention.
Figure 2:
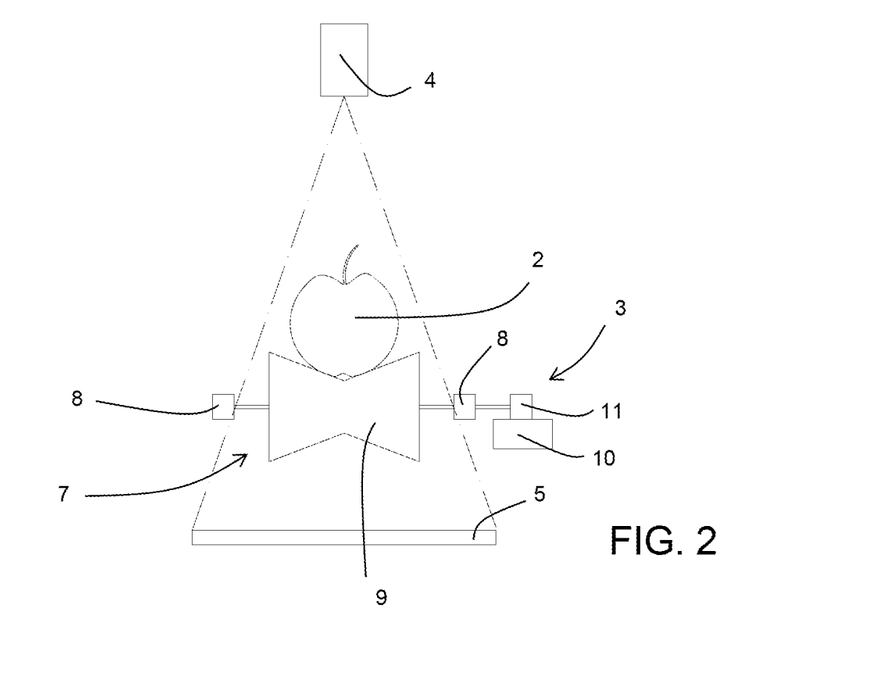
FIG. 2 shows a schematic front view of part of the image shown in FIG. 1.
Figure 3:
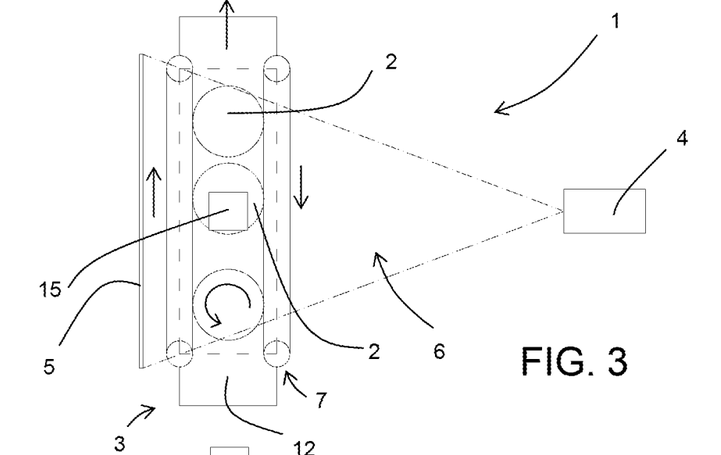
FIG. 3 shows a schematic top view of a second embodiment of a method and of an apparatus according to the present invention.
Figure 4:
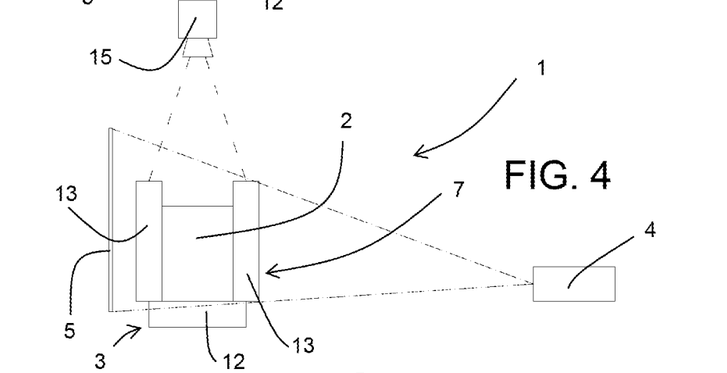
FIG. 4 shows a front view of the embodiment shown in FIG. 3.

In another embodiment, the conveyor 3 comprises at least one movable element, mounted laterally to the motion trajectory and capable of coming into contact with the objects to make them rotate on themselves. By way of example, the mobile element may be a belt, where the object 2 is located, moves in an opposite direction to the advancement direction of the object 2; the contact of the belt against the surface of the object 2 while advancing causes the same result, albeit with a lower rotation speed, can also be obtained using a stationary belt). In the embodiment shown in FIGS. 3 and 4, two movable elements (belts 13) are present, arranged at both sides of the lower conveyor belt 12 and running, respectively, in an opposite direction to the belt, and in the same direction as the belt but at a greater speed (advantageously, the absolute value of the speed difference of the two belts 13 relative to the conveyor belt 12 is the same).

Figure 5:
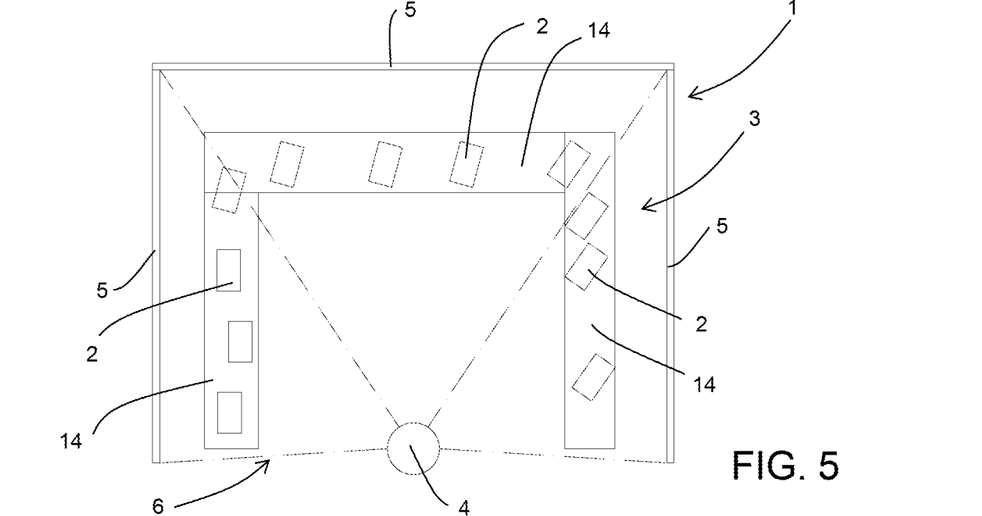
FIG. 5 shows a schematic top view of a third embodiment of a method and of an apparatus according to the present invention.

Finally, in a further embodiment, the conveyor 3 comprises a plurality of distinct successive sections 14 (formed, for instance, by conveyor belts or similar devices), each of which defines a different advancement direction. Advantageously, each section 14 may develop perpendicularly to the previous section. The objects 2 pass from one section 14 to another in an uncontrolled manner, for instance simply by being pushed from the previous section 14 to the next section 14.

In the preferred embodiment, these sections surround a central divergent-beam emitter 4 by at least 180°. By way of example, there may be three sections which, when seen in a plan view, are arranged along three consecutive sides of a rectangle with the emitter 4 placed at the centre of the fourth side and having an irradiation angle of little more than 180°.

Moreover, thanks to the conicity of the x-ray beam, as regards the orientation of the object 2 relative to the x-rays crossing it, the effect of each object 2 simply translating in a straight line along one of the sections is comparable to that which can be obtained on a shorter course by making it rotate on itself.

The present invention offers significant advantages.

Thanks to this invention, it has indeed been possible to develop a method and an apparatus for performing a tomographic examination of an object which can be implemented on an industrial level also in plants that require high productivity and without having to introduce particular structural complications into existing plants.

Finally, it is worth noting that the present invention is relatively easy to make and that the cost associated with its implementation is also not very high.

Many modifications and variations can be made to the invention as designed herein without departing from the scope of the present invention.

All details can be replaced by other technically equivalent details and any materials, shapes and dimensions of the various components may be used according to requirements.

The invention claimed is:

1. A method for performing a tomographic examination of an object (2), comprising the following operational steps:
   an advancement step, during which the object (2) is advanced along a motion trajectory through an examination area (6);
   an irradiation step, in which the examination area (6) is irradiated with x-rays emitted by one or more emitters (4), the position of the one or more emitters (4) being kept fixed relative to the examination area (6), and the x-rays being emitted in propagation directions transversal to the motion trajectory;
   as the object (2) is advanced through the examination area (6), a plurality of detection steps which are performed at successive instants and with one or more fixed x-ray detectors (5) facing the one or more emitters (4), wherein during each detection step the residual intensity of the x-rays which have crossed the object (2) placed in the examination area (6) is detected to obtain, for each detection, a corresponding electronic two-dimensional pixel map related to the density of the object (2) crossed by the x-rays;

a memorisation step, in which each two-dimensional map is memorised in an electronic memory using a computer; and a processing step, in which the two-dimensional maps thus obtained are processed by a computer to obtain a three-dimensional tomographic reconstruction of the object (2); wherein, during the advancement step, there is also a rotation step performed by making or letting the object (2) rotate, at least partly uncontrolled, in such a way that the object (2) rotates around one or more rotation axes which are transversal both to the motion trajectory and to the propagation directions of the x-rays crossing it;

wherein the method also comprises a localisation step performed by a computer and in which it is determined the spatial position in which the object (2) is located relative to the one or more emitters (4) and/or the one or more detectors (5) at the instant when each two-dimensional map is detected;

and wherein the processing step is performed by the computer by factoring in, for each two-dimensional map, the corresponding spatial position of the object (2) as determined in the localisation step.

2. The method according to claim 1, wherein the rotation step is performed in such a way that the object (2) rotates around one or more rotation axes which are inclined at an angle of between 40° and 90° relative to the motion trajectory.

3. The method according to claim 1, further comprising a capturing step, in which a plurality of images of the object (2) are successively captured as it is advanced along the motion trajectory, and wherein the localisation step is performed using the images captured during the capturing step to determine the spatial position in which the object (2) is or was located at the instant when each two-dimensional map is/was detected.

4. The method according to claim 3, wherein, during the localisation step, several successively captured, different images are compared with each other by the computer to determine one or more movements incurred by the object (2), and wherein the one or more movements thus determined are then used to determine said spatial position of the object (2).

5. The method according to claim 4, wherein each movement incurred by the object (2) is determined by identifying, in each image, identical identification features peculiar to the object (2) or applied to the object (2) itself and by using the positions of the identification features in at least two different images to determine a rigid motion performed by the object (2).

6. The method according to claim 1, wherein the localisation step is performed by the computer based on the position, in the two-dimensional maps, of identical identification elements that are x-ray visible, where the identification elements are either peculiar to the object (2) or have been associated with the object (2) itself.

7. The method according to claim 1, wherein the localisation step performed by the computer by performing the processing step several times, each time conjecturing a different sequence of the spatial positions in which the object (2) was located when the two-dimensional maps were detected, and by estimating the precision of each spatial position thus obtained based on the outcome of the processing step, until a desired precision has been obtained.

8. The method according to claim 1, wherein, during the advancement step, the object (2) is advanced along an advancement trajectory lying in a plane and is made or let rotate at least around one rotation axis perpendicular to said plane.

9. The method according to claim 1, wherein, during the advancement step, the object (2) is advanced along an advancement trajectory while rolling on an outer surface of the object itself.

10. An apparatus for performing a tomographic examination of an object, comprising:

a supporting structure;

at least one conveyor (3) capable of advancing an object (2) along a motion trajectory;

one or more x-ray emitters (4), fixed and associated with the supporting structure;

one or more x-ray detectors (5), fixed and facing the one or more x-ray emitters (4), an examination area (6) being defined between the one or more emitters (4) and the one or more detectors (5), through which a part of the motion trajectory develops, the motion trajectory in the examination area (6) being transversal to the propagation directions of the x-rays emitted by the one or more emitters (4) towards the examination area (6);

at least one computer, associated with the one or more detectors (5) to receive from them electronic data corresponding to two-dimensional pixel maps representative of the density of the object (2) crossed by the x-rays, the at least one computer being capable of memorising said two-dimensional maps and being programmed to process the two-dimensional maps in order to obtain a tomographic reconstruction related to the object (2);

means (7) for uncontrolled rotation, associated with the conveyor (3) and configured to cause, as the object (2) is advanced along the motion trajectory, an at least partly uncontrolled rotation of the object (2) in such a way that the object (2) rotates around one or more rotation axes which are transversal both to the motion trajectory and to the propagation directions of the x-rays crossing it;

wherein at least one electronic device is programmed to identify the spatial position in which the object (2) is located relative to the one or more emitters (4) and/or the one or more detectors (5) at the instant when each two-dimensional map is detected;

and wherein the at least one computer is programmed to process the two-dimensional maps in order to obtain a tomographic reconstruction related to the object (2), by factoring in, for each two-dimensional map, the corresponding spatial position of the object (2) as determined by the at least one electronic device.

11. The apparatus according to claim 10, wherein the means (7) for uncontrolled rotation cause, as the object (2) is advanced along the motion trajectory, a rotation of the object (2) around one or more rotation axes which are inclined at an angle of between 40° and 90° relative to the motion trajectory.

12. The apparatus according to claim 10, wherein the electronic device comprises at least one computer, programmed to determine the spatial position in which the object (2) is located at the instant when each two-dimensional map is detected, by processing the two-dimensional maps.

13. The apparatus according to claim 10, wherein the electronic device comprises one or more image capturing devices, facing the examination area (6) and controlled to successively capture a plurality of images of the object (2) as it is advanced along the motion trajectory, and at least one computer, programmed to determine the spatial position in which the object (2) was located when each two-dimensional map was detected, by using the images captured by the one or more image capturing devices.

14. The apparatus according to claim 10, wherein the conveyor (3) comprises a plurality of supports movable along the motion trajectory and wherein a unit for rotating the object (2) is associated with each support.

15. The apparatus according to claim 14, wherein the conveyor (3) comprises at least two motive chains or belts (8), arranged side-by-side and parallel to one another and to the motion trajectory, wherein each support comprises a pair of biconical rollers (9) mounted between the two chains or belts (8) and arranged so that their respective axes are perpendicular to the motion trajectory, and wherein said unit for rotating the object (2) causes the rotation of at least one of the biconical rollers (9).

16. The apparatus according to claim 10, wherein the conveyor (3) comprises a track equipped with rotating rollers or rotating balls, wherein the rotating rollers or rotating balls are arranged and/or actuated at least in groups in a different manner, in order to cause the object (2) to rotate on itself as it is advanced.

17. The apparatus according to claim 10, wherein the conveyor (3) comprises one or more fixed stops, arranged along the motion trajectory to intercept the object (2) as it is advanced and to cause it to rotate on itself.

18. The apparatus according to claim 10, wherein the conveyor (3) comprises at least one movable element (13), mounted laterally to the motion trajectory to come into contact with the objects and make them rotate on themselves.

19. The apparatus according to claim 10, wherein the conveyor (3) comprises a plurality of successive sections (14), each of which defines a different advancement direction, wherein the objects pass from one section to another in an uncontrolled manner, and wherein said sections (14) angularly surround a central divergent-beam emitter (4).

* * * * *